United States Patent [19]

Melink et al.

[11] Patent Number: 5,541,105
[45] Date of Patent: Jul. 30, 1996

[54] METHOD OF CULTURING LEUKOCYTES

[75] Inventors: Georgiann B. Melink, St. Paul; Raji A. Shankar, New Brighton, both of Minn.

[73] Assignee: Endotronics, Inc., Coon Rapids, Minn.

[21] Appl. No.: 233,547

[22] Filed: Apr. 26, 1994

Related U.S. Application Data

[63] Continuation of Ser. No. 998,643, Dec. 30, 1992, abandoned, which is a continuation of Ser. No. 758,191, Sep. 11, 1991, abandoned, which is a continuation of Ser. No. 240,471, Sep. 6, 1988, abandoned, which is a continuation of Ser. No. 856,827, Apr. 28, 1986, abandoned.

[51] Int. Cl.$^6$ ..................................................... C12N 5/08
[52] U.S. Cl. ................. 435/240.242; 435/240.2; 435/240.23; 435/240.241
[58] Field of Search .......................... 424/184.1, 93.71, 424/520; 435/1, 2, 240.2, 240.23, 240.242, 240.1, 240.21, 240.241

[56] References Cited

U.S. PATENT DOCUMENTS

| | | | |
|---|---|---|---|
| 4,364,932 | 12/1982 | Kung et al. | 424/85 |
| 4,391,912 | 7/1983 | Yoshida et al. | 435/241 |
| 4,401,756 | 8/1983 | Gillis | 435/68 |
| 4,404,280 | 9/1983 | Gillis | 435/68 |
| 4,407,945 | 10/1983 | Gillis | 435/68 |
| 4,438,032 | 3/1984 | Golde et al. | 260/112 |
| 4,444,887 | 4/1984 | Hoffman | 435/240 |
| 4,464,355 | 8/1984 | Fabricius et al. | 424/101 |
| 4,473,642 | 9/1984 | Gillis | 435/68 |
| 4,490,289 | 12/1984 | Stern | 260/112 |
| 4,515,893 | 5/1985 | Kung et al. | 435/240 |
| 4,515,894 | 5/1985 | Kung et al. | 435/240 |
| 4,515,895 | 5/1985 | Kung et al. | 435/240 |
| 4,544,632 | 10/1985 | Yamamura et al. | 435/68 |
| 4,690,915 | 9/1987 | Rosenberg | 514/21 |
| 4,804,628 | 2/1989 | Cracauer et al. | 435/240.242 |

OTHER PUBLICATIONS

Mule et al, Science 225 pp. 1487–1489 (1984).
Nabel et al, Cell 23 pp. 19–28 (1981).
Stites, et al. (Editors) Basic & Clinical Immunology, 5th Edition, Lange Medical Publications, Los Altos, Calif., pp. 92–96, 1984.
Lotze, M. T., Transplantation and Adoptive cellular therapy of cancer: the role of T cell growth factors, Cell Trans. vol. 2:33–47, 1993.
Lindemann et al., Lymphokine activated killer cells. Blut vol. 59:375–384, 1989.
Teichmann et al., Susceptibilty of human leukemia to allogeneic and autologous lymphokine-activated killer cell activity: analysis of 252 samples. Nat. Immun. vol. 11:117–132. 1992.

*Primary Examiner*—Margaret Parr
*Assistant Examiner*—Phillip Gambel
*Attorney, Agent, or Firm*—Sughrue, Mion, Zinn, Macpeak & Seas

[57] ABSTRACT

A method for culturing leukocytes includes the culturing of leukocytes in a hollow fiber cartridge perfusion system for at least four days to achieve a harvest yield of at least 100% of leukocytes, the leukocytes having a lytic activity at least equal to that of cells grown in a static culturing system.

11 Claims, 1 Drawing Sheet

METHOD OF CULTURING LEUKOCYTES

This is a continuation of application Ser. No. 07/998,643, filed Dec. 30, 1992, abandoned, which is a continuation of application Ser. No. 07/758,191, filed Sep. 11, 1991, now abandoned, which is a continuation of application Ser. No. 07/240,471, filed Sep. 6, 1988, now abandoned, which is a continuation of application Ser. No. 06/856,827, filed Apr. 28, 1986, now abandoned.

BACKGROUND OF THE INVENTION

1. Field of the Invention

The present invention relates to in-vitro culturing of purified human leukocytes, and in particular, the present invention relates to a method of culturing of purified human leukocytes in a perfusion culturing system.

2. Description of the Prior Art

Attempts to manipulate the immune system with adoptive immunotherapy or by other means has had a long history. A very large number of experimental protocols have been tried in which agents thought to enhance and/or increase immunity have been given to patients. Most of these trials have not been successful and in the few cases in which success has been reported, it has been difficult to reproduce the successful aspects of the trial.

Adoptive immunotherapy in the contents of the present application involves the administration of immunologically active (immunocompetent) cells to an individual. These immunocompetent cells are taken either from the individual to be treated or from another individual. The purpose of administering immunocompetent cells to an individual is to provide a beneficial effect to the patient. For example, in the case of a cancer, cells are provided for the purpose of regressing and/or destroying a cancerous tumor.

Adoptive immunotherapy has been attempted by transferring immunocompetent cells from healthy animals to animals with a cancerous tumor. As such, animal experiments have suggested that an anti-tumor effect can be obtained with a high degree of antigen-specificity in certain tumor models. It has been found that the anti-tumor effect has been limited to certain tumors; and given the antigens-specificity of the effect, it has been assumed that in those cases (where antibodies have been ruled out as the effect or an important media of the effect) that leukocytes which include lymphocytes were involved.

More recently, these leukocytes have been described with reference to their anti-tumor activity and have been referred to as natural killer (NK) and lymphokine-activated killer (LAK) cells. (Other cells of the immune system which may be active in varying degrees regarding anti-tumor immunity also include cytotoxic T lymphocytes (CTL).)

NK and LAK cells are part of the immune system which preferentially lyse and/or kill target cells, including virally-infected and tumor cells. Rosenberg et al have shown in animal models, as well as in man, that lymphocytes obtained from peripheral blood in man or spleen in mouse can be activated within and for a very few days with recombinant interleukin-2 (rIL-2), a factor that activates certain lymphocytes such as LAK cells. Rosenberg has shown that LAK cells will have a regressive effect on tumors both in-vitro and in-vivo. This methodology has been applied to the treatment of cancer in man and encouraging results have been obtained in a significant number of patients, especially those with hypernephroma, melanoma and tumors of the colon.

However, a major difficulty in the protocol of Rosenberg et al has been the growth of the number of cells required to obtain a therapeutic effect. To obtain a therapeutic effect in the patients where a regressive effect on the tumor has resulted between $1\times10^{10}$ and $2\times10^{11}$ LAK cells have been used. Since cells in regular tissue culture (static culture) can only be grown at a maximum of approximately 1 million cells/ml, the amount of tissue culture medium, flasks, incubators and the like needed for the growth of these cells has been enormous. Further, the manipulation of the cells in terms of feeding, removal of waste from the medium and harvesting has been highly labor-intensive. This problem has limited the number of cell preparations that can be readied for treatment of patients and potentially limits the number of treatment centers that could provide such treatment to patients. In addition, the problem of culturing a sufficient number of cells is further intensified if a larger amount of cells would provide a more beneficial treatment and produce better results in patients.

SUMMARY OF THE INVENTION

The present invention is directed to a method of culturing leukocytes wherein the leukocytes are cultured in a perfusion system. Preferably, the leukocytes are cultured in an extracapillary space of a hollow fiber cartridge using a perfusion culturing system. The leukocytes are cultured for at least four days providing a harvestable yield of at least 100% and having lytic activity at least equal to that of leukocytes cultured in a static culturing system.

DETAILED DESCRIPTION OF THE PREFERRED EMBODIMENTS

Figure 1:
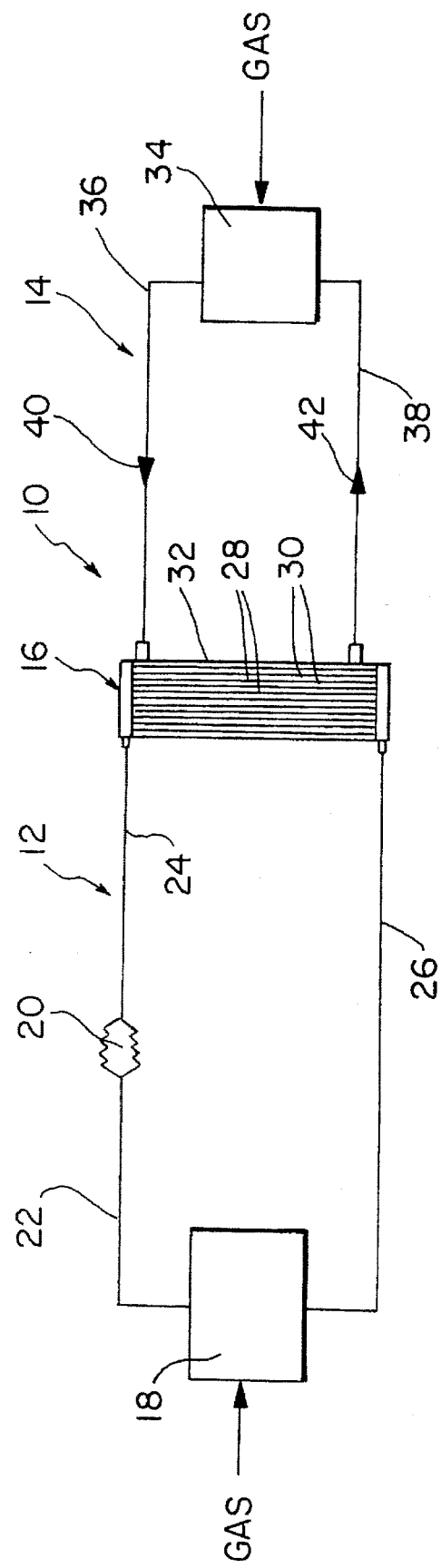
FIG. 1 is a diagrammatical view of a cell culturing system used in the method of the present invention.

The present invention includes a method of culturing leukocytes in a perfusion system such that a harvestable yield of at least 100% of leukocytes having lytic activity is achieved.

By leukocytes is meant white blood corpuscles (cells) that combat infection.

By lymphocytes is meant those leukocytes without cytoplasmic granules. Lymphocytes normally number from 20%–50% of total leukocytes and average 10–12 micrometers in diameter, but may be as large as 20 micrometers. Lymphocytes are characterized by a deeply-staining, compact nucleus taking a dark blue color when using Wright's stain color. The nucleus occupies all or most of the cell, either in the center or at one side. The cytoplasm is usually clear, but in some cells bright red-disk-violet granules are seen.

By monocytes is meant a large mononuclear leukocyte having more protoplasm than a lymphocyte.

By lymphokines is meant those factors which, when presented to lymphocytes, activate the lymphocytes to lytic activity wherein the lymphokine-activated cells lyse and/or kill tumor cells. One example of a lymphokine is recombinant interleukin-2 (rIL-2).

By lytic activity is meant the ability of a cell to destroy a target cell or tumor.

The culturing of cells in hollow fiber cartridges is described in Knazek et al U.S. Pat. Nos. 3,821,087 and 3,883,393. However, limitations have been found in using the hollow fiber cartridges of Knazek et al in terms of achieving maximum cell density in the extracapillary space of the hollow fiber cartridge. Since large numbers of leukocytes are needed for adoptive immunotherapy treatment, high cell densities of leukocytes must be maintained viable and ready for use in such treatment.

The present invention includes the culturing and maintenance of lymphocytes in a hollow fiber cartridge perfusion culturing system such as is described in patent application Ser. No. 658,549 filed on Oct. 9, 1984 and entitled "Improved Hollow Fiber Cell Culture Device and Method of Operation," assigned to the same assignee as the present application, and which is hereby incorporated by reference.

A commercially available hollow fiber cartridge cell culturing system is manufactured and marketed by Endotronics, Inc. of Coon Rapids, Minnesota, U.S.A., under the trademark ACUSYST-P. This culturing system has been on sale for more than one year prior to the filing date of this application.

The ACUSYST-P cell culturing system is diagramatically illustrated in FIG. 1. The system generally indicated at 10 includes a primary media circulation system 12 and a secondary media circulation system 14 for circulating medium within a hollow fiber cartridge 16. The circulation system 12 includes a primary medium supply 18 and a pump 20, preferably a bellows-type pump, connected by tubing 22. The pump 20 is fluidly connected by tubing 24 to the hollow fiber cartridge 16. Tubing 22 and 24 are designated as the supply side of the circulation system 20 supplying medium to the hollow fiber cartridge 16. The hollow fibers or capillaries in the hollow fiber cartridge have membrane walls with a selective molecular weight cut-off of less than approximately 50,000 Daltons and more preferably a cut off of less than approximately 15,000 Daltons. Medium is circulated back to the supply source 18 by tubing 26. The circulation system 12 is fluidly connected to lumens of hollow fibers 28 of the hollow fiber cartridge 16 in a well known manner.

The circulation system 14 supplies medium to the extracapillary space 30 of the hollow fiber cartridge 16, that space being defined as the space between the outer wall surfaces of the hollow fibers and the shell 32 of the hollow fiber cartridge. The circulation system 14 includes a supply source (expansion chamber 34) of medium that supplies medium to the extracapillary space 30 through tubing 36. Medium is returned to the supply source 34 through tubing 38. The tubing 36 and 38, each have mono-directional valves in line so that medium flows in a direction as indicated by arrows 40 and 42.

The supply source 34 is kept at a constant pressure by supplying gas to the source 34. Typically, the gas pressure is kept constant at approximately 100 mmHg above atmospheric. Similarly, the supply source 18 is also pressurized by gas. However, the gas pressure is cycled in supply source 18 from 0 to 100 mmHg above atmospheric. The cycling of the gas pressure produces a changing pressure drop across the membrane walls of the hollow fibers and consequently provides a circulation of the medium within the extracapillary space of the hollow fiber cartridge. Circulation of the medium within the extracapillary space of the hollow fiber cartridge provides for minimization of gradients of nutrients and waste products and minimization and/or elimination of microenvironments and anoxic pockets.

The system 10 is controlled by a digital computer system (not shown) which controls the pump 20 and the gas pressures in both supply sources 18 and 34 and the cycling of the gas pressure in supply source 18.

Using the above-mentioned perfusion system has resulted in yields of leukocytes of greater than 100%. By yield is meant that value obtained by dividing the number of cells initially placed in the hollow fiber cartridge into the number of cells harvested in a sterile condition useful for infusion into a patient. Prior to the present invention, using static culturing techniques, yields on the order of approximately 38%–82% were obtained. (Rosenberg et al.) Consequently, a lesser amount of cells were available for infusion to the patient than had been removed from the patient through leukapheresis. As is easily understood, subjecting an already weakened patient, for example a patient suffering from cancer, to extensive leukapheresis is undesirable. Minimizing the leukapheresis by obtaining an equal or a greater amount of cells through culturing of the cells is highly desirable.

Adoptive immunotherapy is initially started by obtaining leukocytes from blood of the patient by subjecting the blood to leukapheresis. The leukapheresis cell suspension is then centrifuged and the separated leukocytes are harvested, washed and innoculated into the extracapillary space of the hollow fiber cartridge. The cartridges are innoculated with approximately 1.8 to 2.2×10$^9$ cells and the cell culturing system activated to culture the cells.

The cells are cultured with recombinant interleukin-2 (rIL-2) obtained from Cetus Corporation of Emeryville, Calif. to produce a lymphokine-activated killer (LAK) cell.

The LAK cells are then administered intravenously through a venous catheter or by direct infusion into an artery via a percutaneous catheter. The effects of such infusion can be observed on a cancerous tumor by techniques well known in the art. The administration of the LAK cells can be continued until the tumor has totally disappeared or until efforts show no further regression of the tumor. rIL-2 can also be administered in conjunction with the infusion of the LAK cells, depending upon the results observed as to the regression of the tumor and the effect of infusion of the LAK cells into the patient.

The following example is illustrative only and is not intended to limit the present invention. The example is submitted in order to demonstrate more explicitly the method of the present invention.

EXAMPLE 1

The media used in the circulation loop providing media to the lumens of the hollow fibers was RPMI-1640 (Gibco, N.Y.) containing L-glutamine, 1.2 ml/L of a 200 mM solution, and penicillin-streptomycian, 1 ml/L of a 10,000 U/ml, and 10,000 mcg/ml solution (Gibco, N.Y.).

The circulation media for the circulation loop providing media to the extracapillary space included 497 ml of RPMI-1620 medium (Gibco, N.Y.), 90 ml human serum (filtered through 0.45 Um filter), 6 ml penicillin-streptomycian, 7.2 ml L-glutamine, and recombinant interleukin-2 (rIL-2), 3000 U/ml, total units= 1.8×10$^6$ units (Cetus Corporation of Emeryville, Calif.). 500 ml of the medium, having the same composition as the recirculation medium was used to coat the extracapillary space of the hollow fibers in preparation for innoculation of the leukocytes.

A unit of blood (approximately 200 ml) was obtained through leukapheresis. The blood was equally distributed into four 250 ml sterile centrifuge bottles and 5000 U of heparin was added to each bottle (5 ml of a 1000 u/ml solution).

Hanks Buffered Salt Solution without calcium and magnesium were added to bring the volume to 200 ml in each bottle. The leukocytes were centrifuged at 1200 rpm for 15 minutes in a Beckman centrifuge. The supernatant was then discarded and a small volume of hemolytic buffer was added and the cell pellet was resuspended within each bottle with a pipette. The volume was then brought up to 200 ml again with a hemolytic buffer. The cells were again centrifuged at 1200 rpm for 15 minutes.

The supernatant was again discarded and the cell pellet was substantially free of red blood cells. The cell pellet in the bottle was again resuspended with a small amount of Hank's Buffered Salt Solution without calcium or magnesium with a pipette and the volume was brought up to 200 ml with more Hank's Buffered Salt Solution. Any clumps that settled at the bottom of the bottles were drawn out with a pipette.

Again, the bottles were centrifuged at 1200 rpm for 15 minutes and the supernatant was discarded and the cells resuspended in complete RPMI-1640 media (Gibco, N.Y.) containing 15% human serum and 3000 U/ml rIL-2. The concentration of the cells is adjusted to about $8 \times 10^7$ cells per ml and the cells placed in two 60 ml syringes containing approximately 50 ml each of the solution.

The ACUSYST-P feed rate was set to 50 ml per hour. The hollow fiber cartridge was coated 2 to 24 hours prior to innoculation with 500 ml of the coating medium.

The two cartridges were innoculated with 25 ml each of the cells from the two 60 ml syringes via the bypass line and the expansion chamber sample port. Each cartridge was seeded with $1.8-2.2 \times 10^9$ cells having a viability no lower than 95%. The viability of the cells was tested by Trypan Blue Exclusion.

The cells were cultured in a routine manner and by cycling the pressure in the primary circulation system between 0 and 100 mmHg above atmospheric and keeping the pressure in the expansion chamber constant at approximately 100 mmHG above atmospheric.

After culturing, the cells are removed from the hollow fiber cartridge. The cartridges are removed from the ACUSYST-P by clamping off tubing extending from the expansion chamber ports of the cartridge and pulling the tubing off the cartridge and plugging the tubing with sterile plugs. The input and output ends of the cartridge are also clamped and the tubing cut and plugged with sterile plugs at both input and output ends. The cartridge was placed on a ring stand and the tubing from one expansion chamber inlet port is threaded through a master flex pump and connected to a bottle containing 3 liters of RPMI-1640 media. The other tubing segment from the other expansion chamber port was hooked up to a sterile transfer pack. The RPMI-1640 media was pumped into the extracapillary space of the hollow fiber cartridge. Approximately 500 ml containing the lymphocytes is collected into the transfer pack and when the pack is filled, another pack in a sterile fashion is hooked up in its place. This was repeated until no further cells were visually observed in the extracapillary space.

The same procedure regarding removal of the cells was done to the other cartridge.

From a number of cell culturing runs, it was found that yields of greater than 100% were obtained after day four of culturing. In two trials in which the cells were removed from the cartridges on day five, yields of 102% (Trial I) and 150% (Trial II) were obtained. In another trial, in which the cells were cultured for seven days, the yield was 222%. In trials of less than five days, yields of less than 100% were obtained. The yield figure is calculated based on the number of cells seeded in the cartridge and the number of usable cells removed from the cartridge. By usable cells, it is meant those cells having been removed in a sterile fashion and are usable for treating a patient. In the cell culturing process, a number of cells are lost due to the circulation of the media through the extracapillary space in which the cells are being cultured. In addition, a number of cells are lost since all of the cells are not removable in a sterile fashion at the present time from the cartridge.

The cells obtained from Trials I and II were tested for lytic activity and compared to cells cultured in a static culturing system, and in the case of Trial I, lytic activity was also compared to uncultured cells, that is, cells not having been exposed to or cultured with rIL-2. The static cells were cultured in the same type of medium as the ACUSYST-P cultured cells, but for a maximum of four days due to the limitation of static culturing. The target cells used in measuring lytic activity were HL-60 and K562 which are well known in the art. The results of these comparisons are listed in Tables 1 and 2.

TABLE 1

| Ratio Of Effector Cells To Target Cells | Trial 1 | | |
|---|---|---|---|
| | Uncultured | Static Culturing | Present Invention |
| HL-60 | | | |
| 30:1 | 1.7 | 30.9* | 19.3 |
| 10:1 | 2.3 | 28.3 | 22.9 |
| 3:1 | 0.5 | 12.7 | 8.7 |
| 1:1 | 2.3 | 5.3 | 4.6 |
| K562 | | | |
| 30:1 | 1.8 | 37.2* | 47.1 |
| 10:1 | 0.5 | 26.4 | 59.3 |
| 3:1 | 0.7 | 8.7 | 26.3 |
| 1:1 | 1.0 | 2.5 | 9.6 |

*standard deviation greater than 10%

TABLE 2

| Ratio Of Effector Cells To Target Cells | Trial II | |
|---|---|---|
| | Static Culturing | Present Invention |
| HL-60 | | |
| 30:1 | 40.5 | 47.2 |
| 10:1 | 49.6 | 50.5 |
| 3:1 | 20.3 | 35.7 |
| 1:1 | 8.7 | 16.9 |
| K562 | | |
| 30:1 | 67.7* | 68.4 |
| 10:1 | 76.3 | 82.1 |
| 3:1 | 52.8* | 61.0 |
| 1:1 | 34.8 | 37.2 |

*standard deviation greater than 10%

The results in Tables 1 and 2 indicate that the cells cultured according to the present invention have at least equal lytic activity as to cells cultured in a static culturing system. (It should be noted that some values have a standard deviation of greater than 10% and those values are not to be considered in any comparisons.)

Although the present invention has been described with reference to preferred embodiments, workers skilled in the art will recognize that changes may be made in form and detail without departing from the spirit and scope of the invention.

What is claimed is:

1. A method of culturing leukocytes comprising:

culturing leukocytes at a density of about $8\times10^7$ cells per ml in the presence of recombinant interleukin-2, in a hollow fiber cartridge for at least four days to obtain a cell harvest having a yield of at least 100% with respect to the number of cells initially present in the hollow fiber cartridge, wherein the leukocytes cultured have a lytic activity approximately equal to or greater than that of leukocytes cultured in a static culturing system.

2. The method of claim 1, wherein the method comprises culturing the leukocytes in an extracapillary space of said hollow fiber cartridge.

3. The method of claim 2, wherein said method comprises culturing said leukocytes in the presence of said lymphokine by circulating culture medium through the lumens of said hollow fiber cartridge and simultaneously circulating culture medium and said lymphokine through the extracapillary space in said hollow fiber cartridge surrounding said lumens of said hollow fibers and containing said leukocytes.

4. The method of claim 3, wherein said fibers of said hollow fiber cartridge have membrane walls with a selective molecular weight cut off of less than 50,000 Daltons.

5. The method of claim 4, wherein said molecular weight cut off is a cut off of less than 15,000 Daltons.

6. A method of obtaining leukocytes having lytic activity comprising:

obtaining a population of leukocytes from human blood by leukopheresis;

inoculating the population of leukocytes into the extracapillary space of a hollow fiber cartridge culturing system; and culturing the population of leukocytes at a density of about $8\times10^7$ cells per ml, in the presence of a recombinant interleukin-2, for at least four days to obtain a population of cells including leukocytes having a lytic activity, approximately equal to or greater than that of leukocytes cultured in a static culturing system.

7. The method of claim 6, wherein said method comprises culturing said population of leukocytes in the presence of said lymphokine by circulating culture medium through the lumens of said hollow fiber cartridge and simultaneously circulating culture medium and said lymphokine through the extracapillary space in said hollow fiber cartridge surrounding said lumens of said hollow fibers and containing said leukocytes.

8. The method of claim 7, wherein said fibers of said hollow fiber cartridge have membrane walls with a selective molecular weight cut off of less than 50,000 Daltons.

9. The method of claim 8, wherein said molecular weight cut off is a cut off of less than 15,000 Daltons.

10. The method of claim 1, wherein said method comprises said culturing for at least five days to obtain a cell harvest having a yield of at least 150%.

11. The method of claim 6, wherein said method comprises said culturing for at least five days to obtain a cell harvest having a yield of at least 150%.

* * * * *